United States Patent [19]
Sekowski et al.

[11] Patent Number: 6,063,575
[45] Date of Patent: May 16, 2000

[54] ASSAY FOR MEASURING THE ACTIVITY AND FIDELITY OF DNA REPLICATION AND KIT THEREFOR

[75] Inventors: Jennifer W. Sekowski, Bel Air; Linda H. Malkas; Robert J. Hickey, both of Abingdon, all of Md.

[73] Assignee: University of Maryland, At Baltimore, Baltimore, Md.

[21] Appl. No.: 09/045,624

[22] Filed: Mar. 20, 1998

Related U.S. Application Data

[60] Provisional application No. 60/039,381, Mar. 21, 1997.

[51] Int. Cl.[7] ............................... C12Q 1/68; C12P 19/34
[52] U.S. Cl. ........................... 435/6; 435/91.1; 435/91.5; 435/91.52
[58] Field of Search ............................. 435/6, 91.1, 91.5, 435/91.52

[56] References Cited

U.S. PATENT DOCUMENTS

| | | | |
|---|---|---|---|
| 5,574,047 | 11/1996 | Bumol | 514/324 |
| 5,616,461 | 4/1997 | Schaffer et al. | 435/6 |

OTHER PUBLICATIONS

Coll et al Oncology Res. vol. 8 No. 10/11 pp. 435–447, 1996.
Ariza et al Env. & Mol. Mutagenesis vol. 27: 30–33, 1996.
Lin et al, *Proc. Natl. Meet. Am. Assoc. Cancer Res.*, 37:A3413 (1996).
Sekowski et al, *Proc. Natl. Meet. Am. Assoc. Cancer Res.*, 38:A270 (1997).
Coll et al, *Proc. natl. meet. Am. Assoc. Cancer Res.*, 37:A3409 (1996).
Sekowski et al, *Cancer Res.*, 58:3259–3263 (1998).
Bechtel et al, *Cancer Res.*, 58:3264–3269 (1998).
Coll et al, *Oncology Res.*, 9:629–639 (1997).
Sekowski, J.W., et al., "Mercuric Ion Inhibits the Activity and Fidelity of the Human Cell DNA Synthesome" *Toxicol. Appl. Pharmacol.* 145:268–276, 1997.
Malkas, L.H., et al., "A21S Enzyme Complex from HeLa Cells That Functions in Simian Virus 40 DNA Replication in Vitro" *Biochemistry* 29:6362–6374, 1990.
Malkas, L.H., et al., "Sequence recognition protein for the 17–base–pair A+T–rich tract in the replication of origin of simian virus 40 DNA" *Proc. Natl. Acad. Sci. USA* 86:70–74, 1989.
Hickey, R.J., et al., "Multienzyme Complex for DNA Replication in HeLa Cells" In: Moses, R.E.; Summers, W.C., eds. *DNA Replication and Mutagenesis* Washington, D.C.; American Society for Microbiology; pp. 41–54, 1988.
Mikita, T., et al. "Functional Consequences of the Arabinosylcytosine Structural Lesion in DNA" *Biochemistry* 27:4698–4705, 1988.
Roberts, J.D., et al., "The fidelity of a human cell DNA replication complex" *Proc. Natl. Acad. Sci. USA* 85:7064–7068, 1988.
Murakami, Y., et al. "Species–specific in vitro synthesis of DNA containing the polyoma virus origin of replication" *Proc. Natl. Acad. Sci. USA* 83:6347–6351, 1986.

*Primary Examiner*—Kenneth R. Horlick
*Assistant Examiner*—Jeffrey Siew
*Attorney, Agent, or Firm*—Sughrue, Mion, Zinn, Macpeak & Seas, PLLC

[57] ABSTRACT

Mercuric ion is cytotoxic and mutagenic to cells. However, the mechanisms of mercuric ion-induced cytotoxicity are not well understood. Studies have suggested that these effects may be due in part to the alteration and inhibition of a variety of cellular processes including DNA replication, DNA repair, RNA transcription, and protein synthesis. However, prior art studies utilizing whole cells, cell extracts, or purified DNA polymerases to examine these activities are not able to specifically identify the precise mechanism or site of the effect or adequately represent the highly ordered environment in which DNA replication occurs in the intact cell. We disclose a novel method for measuring the activity and fidelity of DNA replication using the complex of proteins called the DNA synthesome, an isolated multiprotein form of DNA polymerase. The DNA synthesome is a highly organized complex of proteins capable of supporting all phases of SV 40 origin-specific DNA replication in vitro. The assay and kit described herein can be used both to examine the mechanism of cytotoxicity and mutagenicity and to identify compounds that alter the activity and fidelity of the DNA synthetic apparatus such as heavy metal ion, particularly mercuric ion. The assay and kit can be used to rapidly screen compounds for toxic activity.

11 Claims, 6 Drawing Sheets

ASSAY FOR MEASURING THE ACTIVITY AND FIDELITY OF DNA REPLICATION AND KIT THEREFOR

CROSS-REFERENCE TO RELATED APPLICATIONS

This application is an application filed under 35 U.S.C. §111(a) claiming benefit pursuant to 35 U.S.C. §119(e) (1) of the filing date of Provisional Application No. 60/039,381, filed Mar. 21, 1997, pursuant to 35 U.S.C. §111(b).

The development of the present invention was supported by the University of Maryland, Baltimore, Md. and by funding from the National Institutes of Health (Contract Nos. NIH CA-57350 and NIH CA-65754) and the United States Army (Contract No. DAMD 17-94-J4151). The United States Government has a non-exclusive, irrevocable, paid-up license to practice or have practiced for or on behalf of the United States the invention herein as provided for by the terms of the above mentioned contracts awarded by the United States Government.

FIELD OF THE INVENTION

The invention generally relates to an in vitro method for measuring the fidelity of DNA replication. The invention specifically relates to a fidelity assay that may be used to identify toxins, particularly mutagenic compounds. The method relies on detecting perturbation of mammalian cellular DNA replication using the DNA synthesome complex.

BACKGROUND OF THE INVENTION

Mercuric ion is extremely cytotoxic to both procaryotic and eucaryotic cells (Umeda et al., 1969; Umeda and Nishimura, 1979; Cantoni et al., 1982; Goldberg et al., 1983; Cantoni et al., 1984). In humans, mercuric ion is known to accumulate in the thyroid gland and to potentially lead to the formation of pre-malignant and malignant thyroid nodules (Zaichick et al., 1985). The precise mechanism(s) mediating the carcinogenic effects of mercuric ion is not well defined, but appears to be related to the ingestion or inhalation of the metal, conversion of the metal to mercuric ion, and the translocation of the ion to the thyroid (Zaichick et al., 1985). Part of the cytotoxic and carcinogenic effects of mercuric ion may be due to the ability of the metal ion to alter the DNA synthetic machinery of the cell (Goldberg et al., 1983; Robinson et al., 1984; Williams et al., 1986). Alterations of the activity of the DNA replication machinery are suggested to have a role in mediating the mutagenic effects of mercuric ion (Ariza and Williams, 1996).

Mercuric ion has been reported to alter both the extent of DNA synthesis and the type of DNA replication formed in experiments using intact mammalian cells, (Ariza and Williams, 1996; Robinson et al., 1984; Oberly et al., 1982; Christie et al., 1984), crude mammalian cell extracts, (Oberly et al., 1982; Robinson et al., 1984) and purified enzymes (Caldentey et al., 1992; Williams et al., 1986; Oberly et al., 1982; Niyogi et al., 1981; Hsie et al., 1979). In addition, studies using purified bacterial phage DNA polymerase P1 is strongly inhibited by mercuric ion (Cladentey et al., 1992). The inhibition of DNA polymerase activity by mercuric ion is postulated to be at least partially responsible for the observed inhibition of intact cell DNA synthesis. Furthermore, mercuric ion not only inhibits the activity of the DNA polymerase, but alters the fidelity with which DNA synthesis is carried out by this polymerase.

In vitro mutagenesis assays utilizing purified *E. coli* DNA polymerase have demonstrated that several divalent metals, which are known to be carcinogenic (e.g. lead, cadmium, and nickel) produce significant increases in the number of nucleotide misincorporations during the DNA synthesis process (Sirover and Loeb, 1976; Miyaki et al., 1977; Sirover et al., 1979; Tkeshelashvili et al., 1979; and Tkeshelashvili et al., 1980). Because mercuric ion is also a suspected carcinogen and is a member of the group BII elements, which also contains cadmium ion, we decided to examine whether the mercuric ion could potentially act as a carcinogen by altering the activity of the DNA synthetic machinery of the cell.

Mercuric ion has-been postulated to use one or more of the following mechanisms to alter the fidelity of the DNA synthesis process. First, mercuric ion can alter substrate conformation (i.e. through metal-nucleotide interaction); second, it can alter the conformation of proteins essential for replication and for repair (Williams and Crothers, 1975) (i.e. through metal-protein interactions); third, mercuric ion can alter template-base specificity, (Zakour et al, 1981). Mercuric ion also exhibits two properties which dramatically contribute to the development of alterations contained in cells exposed to mercuric ion. First, mercuric ion has been shown to have potent DNA strand scission activity (Cantoni et al., 1989; Robinson et al., 1984; and Williams et al., 1986). This property allows the ion to induce changes in the DNA template which can alter the ability of the DNA replication machinery to bind to the template properly. This disruption in template binding is also postulated to distort at least some of the components of the replication machinery, and subsequently alter the binding of deoxynucleotides by DNA polymerase and cause misincorporation of nucleotides into the growing DNA strand. Second, mercury has a strong affinity for thiol bonds, which are present in virtually all of the replication proteins, and many other cellular enzymes (Hayes, 1983). The binding of mercuric ion to these thiol groups can severely distort the structural integrity and activity of these proteins. To examine whether mercuric ion can alter the activity and fidelity of the DNA synthetic apparatus of human cells we isolated the cellular DNA synthesizing machinery from human cervical cancer cells (HeLa) and tested the effects of a range of mercuric ion concentrations on in vitro DNA replication activity, DNA polymerase activity, and fidelity with which this complex carries out DNA synthesis.

We chose to use the isolated DNA synthetic machinery from HeLa cells for these studies because our characterization of this highly organized complex of proteins (which we have termed the DNA synthesome) (Lin et al., 1996) indicated that the DNA synthesome contained DNA polymerases α and δ. The synthesome is fully competent to support all phases of simian virus 40 (SV40) origin-specific DNA replication in vitro (Malkas et al., 1990). The biochemical characterization of this isolated multiprotein form of DNA polymerase has resulted in the identification of several protein components of the synthesome. These proteins include: DNA polymerases α, δ, ε, DNA primase, topoisomerases I and II, proliferating cell nuclear antigen (PCNA), replication factor C (RFC), replication protein A (RPA), DNA helicase, DNA methyltransferase, poly(ADP) ribose polymerase and DNA ligase I (Malkas et al., 1990; Applegren et al., 1995; Coll et al., 1996). In addition, the DNA replication process mediated by the human cell synthesome in vitro has been shown to exhibit all of the features of the replication process as is carried out by intact cell (Malkas et al., 1990; Applegren et al., 1995). The DNA synthesome has been isolated and characterized from human and murine cells (Malkas et al., 1990; Applegren et al., 1995;

Wu et al., 1994), human breast tissue cells and primary human breast tumors (Coll et al., 1996), from human leukemia cells (Lin et al., 1996), and from human pancreatic cells (Hickey, unpublished data). Our model describing the DNA synthesome is based on the sedimentation and chromatographic profiles of the individual proteins found to co-purify with one another as a fully functional DNA replication complex (Wu et al., 1994; Applegren et al., 1995; Coll et al., 1996).

The results presented here strongly suggest that the human DNA synthesome can serve as a useful and highly novel in vitro model system for testing whether heavy metal ions can directly induce changes in the activity and fidelity of the cellular DNA synthetic apparatus.

SUMMARY OF THE INVENTION

It is an object of the invention to provide a means and method for measuring the fidelity of DNA replication It is the object of the invention to provide a method and means for rapidly screening compounds for toxic and/or mutagenic activity.

The means and method involve detecting perturbation of mammalian cellular DNA replication using the complex of proteins called the DNA synthesome, an isolated multiprotein form of DNA polymerase. The DNA synthesome is a highly organized complex of proteins capable of supporting all phases of SV 40 origin-specific DNA replication in vitro.

It is a further object of the invention to provide a means and method for examining the mechanism behind the cytotoxicity and mutagenicity associated heavy metal ion exposure, more specifically mercuric ion exposure.

BRIEF DESCRIPTION OF THE DRAWINGS

FIG. 1A: Depicts the effect of a range of mercuric chloride concentrations on DNA synthesome-mediated in vitro DNA replication. In vitro DNA replication reactions were performed using the protocol described herein, in the absence and presence of a range of concentrations of mercuric chloride (test toxin: ■, plus T-antigen DNA synthesis; □, minus T-antigen DNA synthesis) or sodium chloride (control: Δ, T-antigen dependent DNA synthesis). The values depicted are the average of three independent assays. The average of two control reactions carried out in the presence of various concentrations of sodium was used to calculate the specific activity of the control treated DNA synthesome. The positive control values fell between 95 and 10% of the specific activity observed in DNA replication reactions carried out in the absence of metal salts. Reactions conducted in the presence of sodium chloride served as a positive control for comparing the effect of chloride ion on in vitro DNA synthesis. The mean specific activity of two control reactions deviated less than 3% from each other. The units of sodium chloride (control) specific activity represent the T-antigen dependent activity (units of DNA replication activity in the presence of T-antigen minus the units of DNA replication activity in the absence of T-antigen)

FIG. 1C: Depicts the effect of mercuric chloride on DNA template integrity. The interaction of mercuric ion and template DNA was examined using the strand scission assay described herein. Mercuric chloride concentrations were indicated for each land: Lane 1=0 $\mu$M; Lane 2=2 $\mu$M; Lane 3=10 $\mu$M; Lane 4=25 $\mu$M; Lane 5=50 $\mu$M, Lane 6=75 $\mu$M; Lane 7=100 $\mu$M; Lane 8=123-bp marker (Sigma Co.).

FIG. 2: Depicts the effect of a range of concentrations of mercuric chloride and sodium chloride on intact cell DNA synthesis. In tact cell DNA synthesis assays were performed using the protocol described herein, in the presence and absence of a range of concentrations of mercuric chloride (■). The values reported are the average of three independent assays. Control reactions were carried out in the absence of metal salts. The value for the incorporation of [$^3$H] thymidine into acid-insoluble material from individual cultures of cells containing 1×10$^5$ cells/plate deviated from one another by less than 3% and were used to calculate the percent inhibition of [$^3$H] thymidine incorporated into the cells incubated with each of the indicated concentrations of mercuric chloride. HeLa cells were seeded at a density of 5×10$^4$ per 60-mm cell culture plate. Twenty four hours later the cultures were incubated with several concentrations of mercuric chloride (1, 4, 8, 10, 25, 50, 75, and 100 $\mu$M) for periods of up to 8 hr. At the time intervals indicated, the cultures were labeled for 1 hr with [$^3$H] thymidine (1 $\mu$Ci/ml) in fresh media, after which the cells were washed three times with PBS and lysed, and the level of nucleotide incorporated into DNA was measured by liquid scintillation counting as described by Horwitz, 1971. The level of intact cell DNA synthesis is expressed as a percentage of the level of DNA synthesis observed in cells incubated in 1 mM sodium chloride. the results shown in this figure are the average of three separate experiments; error bars denote the standard of the mean.

FIG. 3: Depicts bacterial colony formation and detection of colonies expressing a defective β-galactosidase gene. The following plates are representative of results obtained in the forward mutagenesis assay: (A) no metal=1 mutant per 4.5×10$^3$ transformants=0.02% mutant frequency; (B) 2 $\mu$M HgCl$_2$=3 mutants per 850 transformants=0.14% mutant frequency; (C) 50 $\mu$M HgCl$_2$=5 mutants per 700 transformants=0.86% mutant frequency; (D) 100 $\mu$M HgCl$_2$=11 mutants per 400 transformants=1.48% mutant frequency.

DETAILED DESCRIPTION OF THE INVENTION

Methods and Materials

Cell culture and harvest. Suspension cultures of HeLa cells were grown in Joklik's modified Eagle's medium supplemented with 5% each of irradiated calf and newborn bovine serum. Exponentially growing cells ($5 \times 10^5$ cells/ml of medium) were harvested and washed three times with phosphate-buffered saline (PBS): 8.4 mM $Na_2HPO_4$, 137 mM NaCl, 2.7 mM KCl, 1.5 mM $KH_2PO_4$. The cells were then pelleted by low-speed centrifugation (200×g, 5 min, 4° C.) and the cell pellets were stored at −80° C. prior to initiating the isolation of the DNA synthesome.

Monolayer cultures of HeLa cells were grown in DME containing 5% each of irradiated calf and newborn bovine serum. The cultures were maintained at 37° C.

Preparation of the DNA synthesome. The HeLa cell DNA synthesome was isolated as described by Malkas et al., 1990. The protein fraction designated Q-Sepharose (Malkas et al., 1990), which contains the DNA replication-competent synthesome, was used in the experiments described in this report.

Preparation of the SY40 large T-antigen. The SV40 large T-antigen protein was prepared as described previously by Sinmianis and Lane (1985).

Measurement of intact cell DNA synthesis. Monolayer cultures of $0.5 \times 10^5$ HeLa cells were seeded in 60 mm cell culture dishes and allowed to grow overnight. The stock concentrations of mercuric chloride to be tested were dissolved in 18.3 Megaohm MilliQ $H_2O$ and then added to the cell cultures to yield final concentrations of 1–100 µM. Following 2, 4, 6 or 8 hours of exposure to the mercuric chloride, $^3$H-thymidine was added to individual cell cultures, and the amount of $^3$H-thymidine incorporated into macromolecular material in 1 hour was determined as described by Horwitz et al. (1971).

In vitro DNA Replication Assay. The reaction mixtures (50 µl) contain 30 mM HEPES (pH 7.8), 7 mM $MgCl_2$, 0.5 mM DTT, 50 µM dATP, 100 µM each of dGTP, dCTP, dTIP, either 5 µCi [α-$^{32}$P]dCTP (4,000 cpm/pmol) or 100 µM dCTP, 200 mM each of CTP, TIP, GTP, 4 mM ATP, 40 mM phosphocreatinine, 100 µg of creatinine phosphokinase, 15 mM sodium phosphate (pH 7.5), 30 ng of the plasmid pBK-CMV, and approximately 1.0 µg of large T-antigen. The reaction mixture is incubated at 37° C. for 3 hours. After 3 hours, 10 µl of the reaction mixture is pipetted onto Whatman DE81 filters and allowed to air-dry. The filters are then washed 1×(5 min.) with 0.1 M NaPPi buffer (pH 7.0), and 3×(5 min.) with 0.3 M ammonium formate (pH 7.4), air-dried, and counted in a liquid scintillation counter (30).

DNA polymerase assay. DNA polymerase activity was measured as described by Malkas et al., 1990.

Precipitation of the newly replicated DNA. Following the spotting of 10 µl of the reaction mixture onto DE81 filters, the DNA in the remaining 40 µl of assay mixture was isolated from each in vitro DNA replication reaction as described by Malkas et al., 1990. The resulting isolated DNA was treated with DpnI (0.02 U, 30 min.) to remove any unreplicated plasmid template DNA present in the reaction mixture, and after the digestion of non-replicated template DNA, the replicated plasmid surviving digestion was extracted using the phenol/chloroform extraction procedure described by Sambrook et al., 1989. The extracted DNA was precipitated by the addition of ammomium acetate to a final concentration of 0.2 M along with 2 volumes of 100% isopropanol. After centrifugation at 12,000 rpm (14,956× g), the resulting DNA pellets were washed 3× with 70% ethanol, air-dried or dried in a speed-vacuum, and then resuspended in 20 µl TE buffer (10 mM Tris-HCl, pH 8.0/1 mM $Na_4$ EDTA).

Forward Mutagenesis Assay: Transfection and Plating. The forward mutagenesis assay employed by our laboratory uses a DNA template, pBK-CMV, for which we have not been able to detect any spontaneous mutations following analysis of greater than $8.0 \times 10^4$ colonies (Sekowski and Hickey, unpublished data) Thus, the spontaneous mutation rate is approximately $10^4$ fold lower than that of the M13 phage (which is typically $2-5 \times 10^{-4}$ mutant nucleotides).

The in vitro replicated pBK-CMV DNA recovered following Dpn I digestion was used to transform electrocompetent E. coli host cells (XL-1 Blue MRF'). The transformation was carried out by the addition of 60 µl of electrocompetent bacteria (approximately $6.0 \times 10^9$ cells) to approximately 200 ng of Dpn I treated pBK-CMV (10 µl). The mixture was incubated for 10 minutes on ice before electroporating the cells (at a setting of 1.4 kV, 25 µF, and 200 ohms) in a Bio-Rad Gene Pulser apparatus. Immediately following the electroporation, 1 ml of chilled sterile SOC buffer (20 mM glucose in LB media) was added to the electroporation cuvette. The electroporated mixture was then incubated on ice for 10 minutes, and then in a rotary shaker (250 rpm) at 37° C. for 1 hour. An amount of the culture sufficient to yield 500–1,000 bacterial colonies per plate was plated onto 20 ml of LB agar containing 1.25 mg kanamycin, 4 µl IPTG (200 mg/ml) and 40 µl X-gal (20 mg/ml). These plating conditions give intense blue color for the wild-type plasmid which facilitates the visualization of mutant phenotypes. The mutant colonies range from pure white to intermediate (light blue) phenotypes.

Scoring of Mutants. The inactivation of the α-complementation gene (the product of which is the catalytic subunit of β-galactosidase), due to a mutation in the lac Zα gene in pBK-CMV, gives a variety of mutant phenotypes, resulting from the lack of a fully functional β-galactosidase gene product. These mutant phenotypes were scored after incubating the plates at 37° C. for approximately 12–15 hours. Using the plating conditions described above, expression of the wild-type pBK-CMV DNA in the E. coli host generates a dark blue bacterial colony. Bacterial colonies expressing the mutated pBK-CMV plasmid express an altered β-galactosidase gene, which can be distinguished from those colonies expressing the wild type plasmid, by their light blue to yellowish white color phenotypes. In order to reproducibly and precisely score the variable mutant phenotypes, only the pure white colonies (i.e. colonies lacking any trace of blue or green color) were scored as mutant.

Reagents. Creatinine phosphokinase, phosphocreatinine, and all of the inorganic metal salts were purchased from the Sigma Chemical Co. The ribonucleotides and deoxyribonucleotides used in the assays were purchased from Pharmacia Biotechnology Inc., and the radiolabeled nucleotides used in our assays ($^3$H-thymidine, 20 Ci/mmole; $^3$H-dTTP, 20 Ci/mmole, and $^{32}$P-dCTP, 3000 Ci/mmole) were purchased from DuPont-New England Nuclear.

RESULTS

Figure 1A:
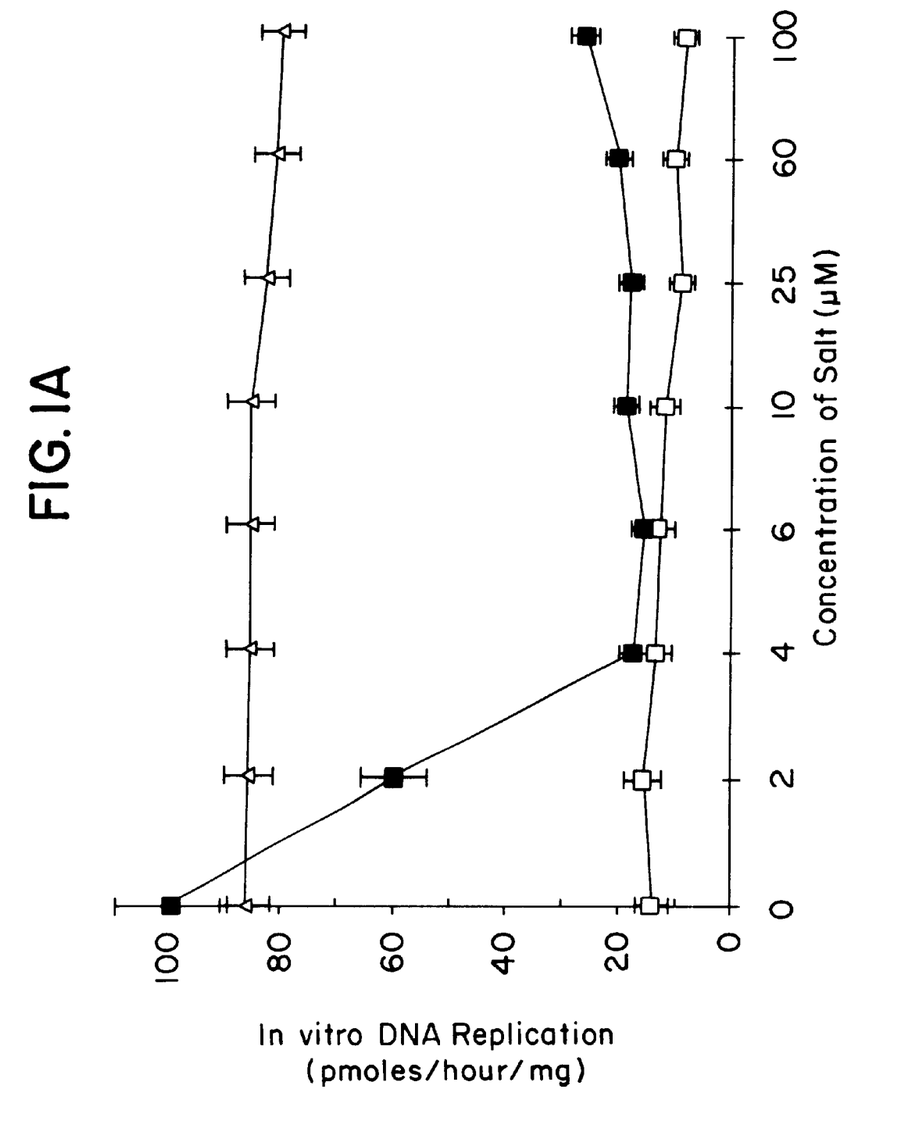

Mercuric ion inhibits in vitro DNA replication (FIG. 1A, Table I). To determine whether mercuric ion can directly affect the ability of the isolated human cell DNA synthesome to support in vitro DNA synthesis, we performed DNA synthesome-mediated in vitro DNA replication assays in the absence and presence of a variety of mercuric ion concentrations (Materials and Methods). The results of these experiments (shown in FIG. 1a) demonstrate that even low concentrations of mercuric ion significantly inhibit DNA synthesome-mediated DNA replication in vitro. For example, reactions performed in the presence of 2 μM mercuric ion inhibited DNA replication by more than 50% of the level of replication reactions performed in the absence of mercuric ion. When higher concentrations of mercuric ion (4, 6, and 10 μM) were added to the in vitro DNA replication reaction, the level of DNA replication decreased by more than 90%. These results suggest that mercuric ion can directly affect the ability of the synthesome to carry out DNA replication in vitro.

To verify that the inhibition of synthesome-driven DNA replication was due solely to the interaction of the mercuric ion with the synthesome and not to the chloride component of the salt or the divalent character of mercuric ion, we performed in vitro DNA replication reactions in the presence of various concentrations of sodium, zinc or nitrate ions (Table I). Our results indicate that sodium chloride did not significantly inhibit in vitro DNA replication (i.e., less than 5% inhibition) at the concentrations tested. It was also observed that sodium nitrate had little effect on synthesome-driven DNA replication over the range of concentrations examined. To determine whether the effect of mercuric ion on in vitro DNA replication could be attributable to the divalent nature of the mercuric ion, we added zinc chloride to the replication reaction. We observed that zinc chloride slightly inhibited in vitro DNA replication at the highest concentration tested (100 μM). Inhibition of the DNA synthesome-mediated in vitro DNA replication by 100 μM zinc chloride was only about 5% greater than that observed in reactions run in the presence of 100 μM sodium chloride or sodium nitrate, and though statistically significant, the decrease in synthetic activity ran well within the expected experimental error for the assay. Taken together, these results suggest that the effects of mercuric ion on synthesome-mediated DNA replication are due specifically to the mercuric ion itself, and not the counter ion or the divalent character of the metal ion.

TABLE 1
Effect of sodium chloride, sodium nitrate, and zinc chloride on DNA synthesome-mediated in vitro DNA replication.

TABLE 1

Effect of sodium chloride, sodium nitrate, and zinc chloride on DNA synthesome-mediated in vitro DNA replication.
Percent Control Incorporation of $^{32}$P-dCTP[a–c]

| μM | NaCl | NaNO$_3$ | ZnCl$_2$ |
|---|---|---|---|
| 1 | 100 | 100 | 100 |
| 10 | 97 | 98 | 93 |
| 100 | 96 | 96 | 92 |

[a]DNA replication assays were conducted as described in the Materials and Methods in the absence or presence of the metal salts indicated.
[b]Percent inhibition was calculated relative to reactions performed in the absence of exogenously added salts.
[c]The values reported represent the average of three independent assays conducted at each of the indicated salt concentrations. These values deviated from the average by no more than 3%.

Figure 1B:
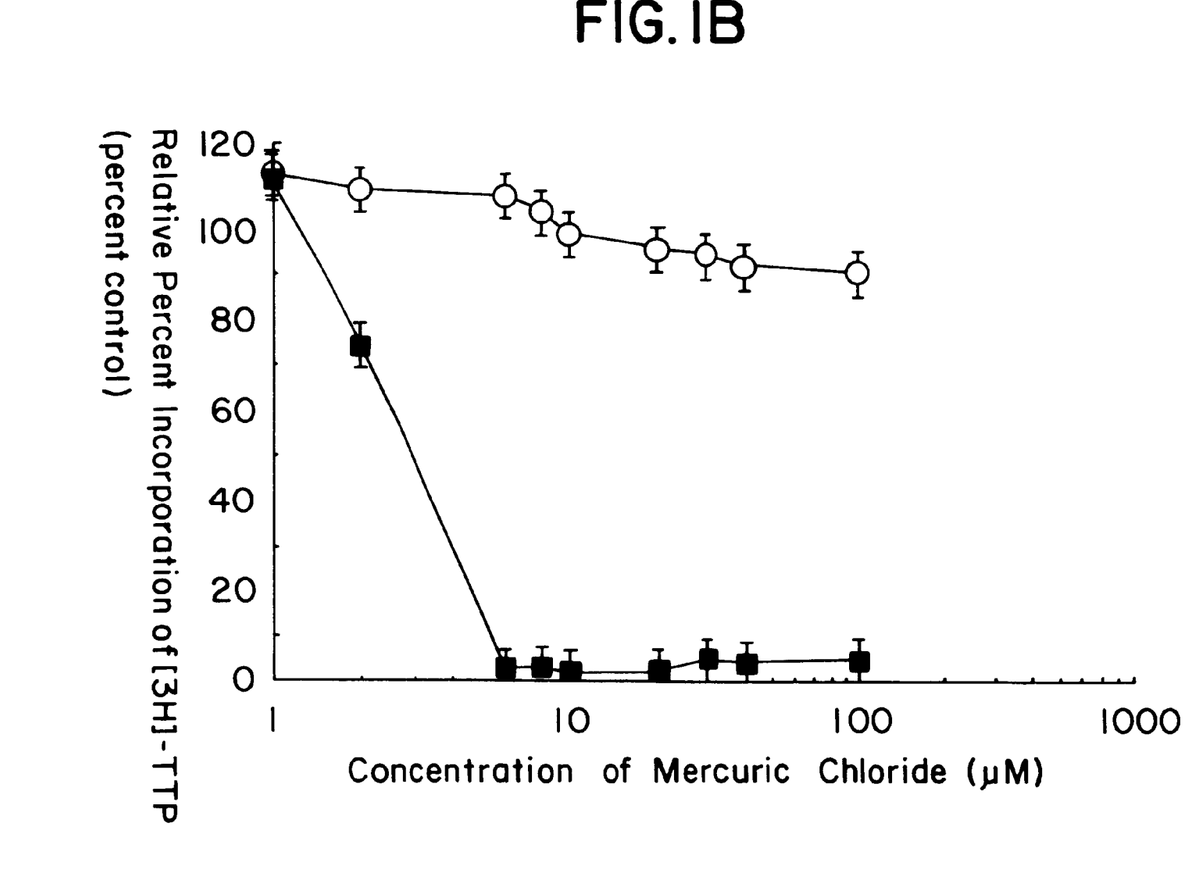
FIG. 1B: Depicts the effect of a range of mercuric chloride concentrations on DNA synthesome-associated DNA polymerase activity. The DNA synthesome-associated DNA polymerase activity reactions were performed using the protocol described herein, in the absence and presence of a range of concentrations of mercuric chloride in the absence and presence of a range of concentrations of mercuric chloride (test toxin:■) or sodium chloride (control: ○). The values depicted are the average of three independent assays. The average of two control reactions carried out in the absence of metal salts was used to calculate the activity of the nontreated DNA synthesome.
Figure 1C:
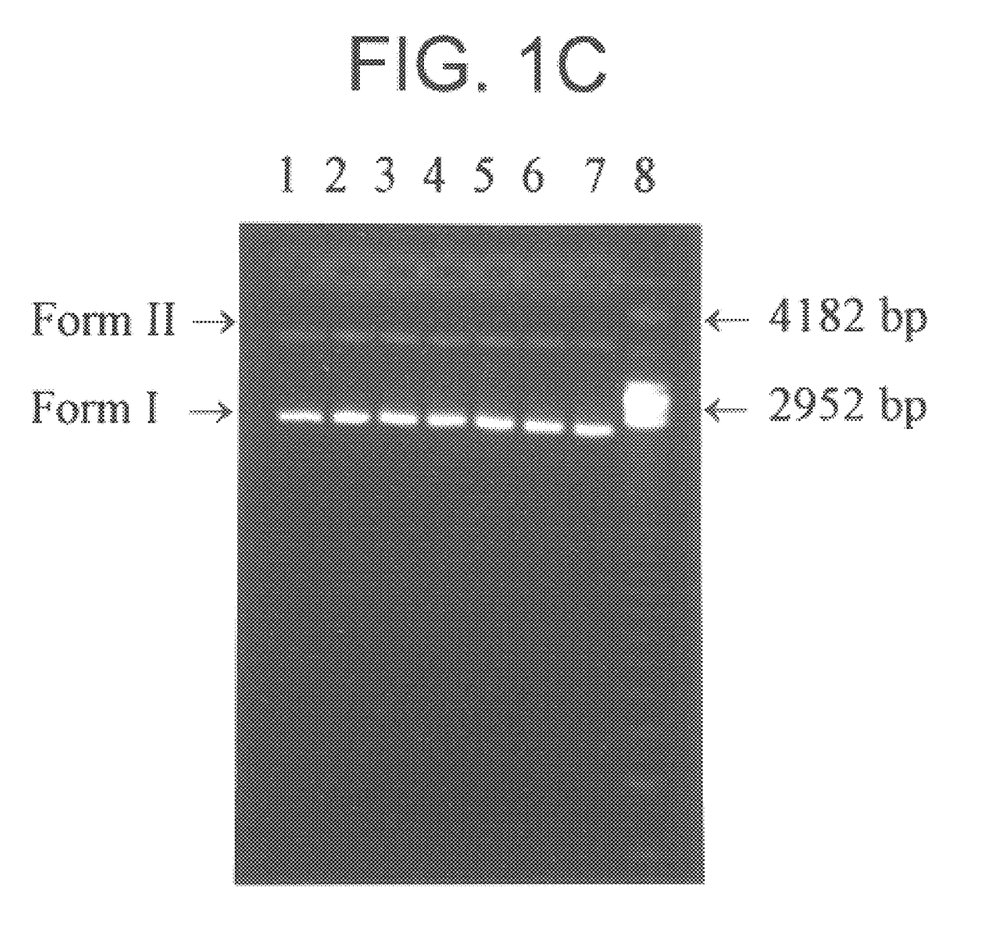

Mercuric ion inhibits synthesome-associated DNA polymerase activity in a manner that mirrors the inhibition of synthesome-mediated in vitro DNA replication (FIG. 1b). A recent report has suggested that mercuric ion inhibits DNA polymerase activity (Caldentey et al., 1992). We initiated studies to investigate whether mercuric ion would inhibit the activity of synthesome-associated DNA polymerase. DNA synthesome-associated polymerase activity of the DNA synthesome was measured in the absence of mercuric chloride and in the presence of various concentrations (1–100 μM) of mercuric chloride (FIG. 1B). Inhibition of DNA polymerase activity below that of the no metal control began at 2 μM mercuric ion. Over 95% of the DNA polymerase activity inhibition was exhibited at concentrations of mercuric ion in excess of 2 μM. Very low concentrations of mercuric ion (1 μM) and sodium ion (2–6 μM) appears to slightly stimulate DNA synthesome-associated polymerase activity.

We also observed that the DNA synthesome-associated DNA polymerase activity was only slightly affected by sodium chloride in excess of 40 μM; resulting in an inhibition in the activity of the DNA polymerase of less than 10% as compared to the no metal control. The inhibitory effects of mercuric ion on the activity of the DNA synthesome-associated DNA polymerase are therefore specifically attributable to the heavy metal ion, and closely parallel the mercuric ion induced inhibitory profile observed for synthesome-mediated in vitro DNA replication.

Figure 2:
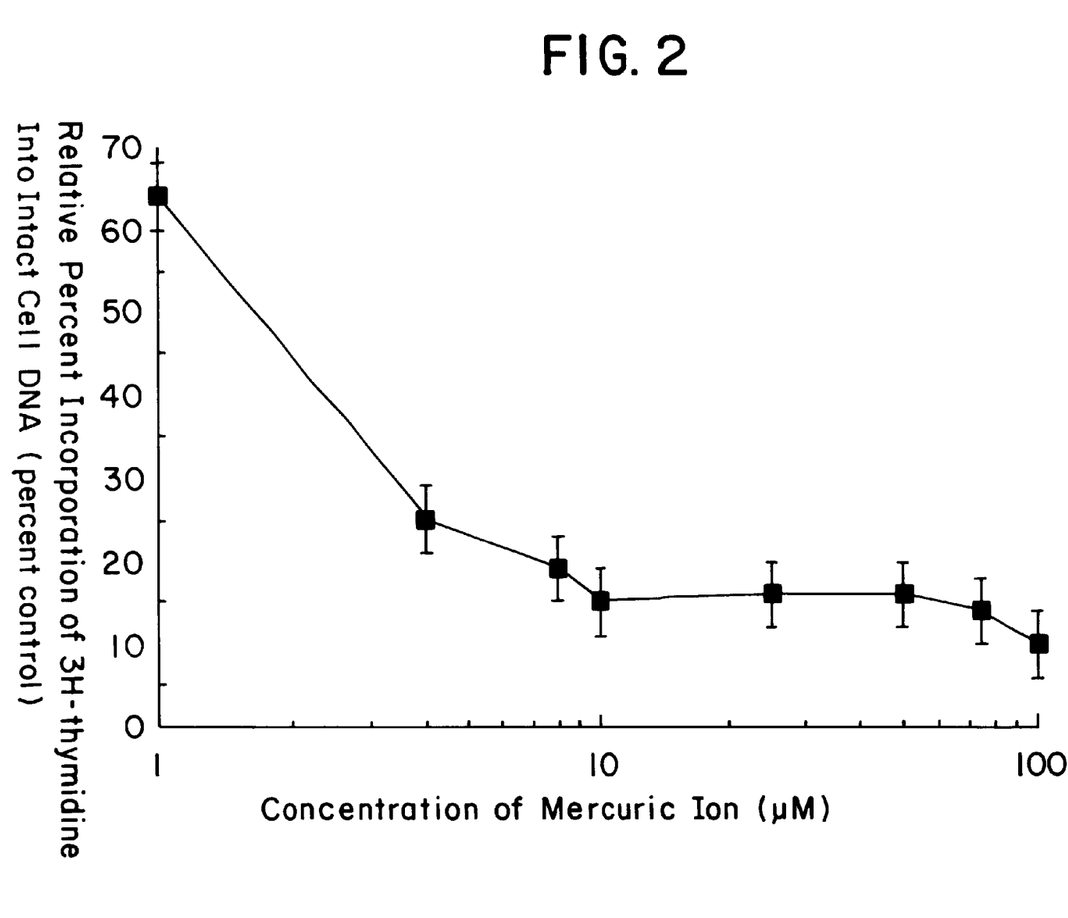
Figure 3A:
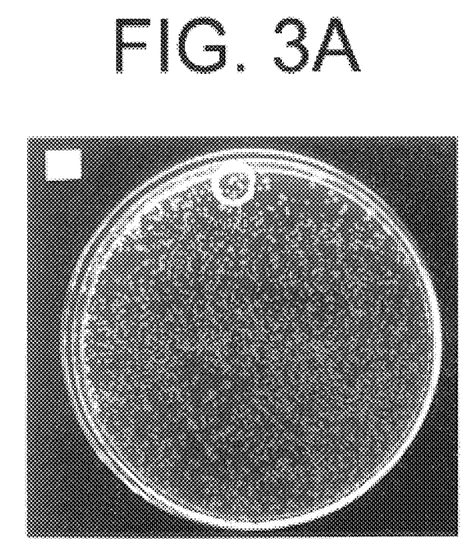
Figure 3B:
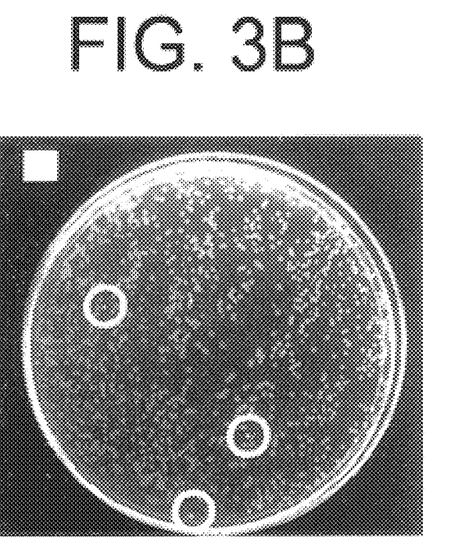
Figure 3C:
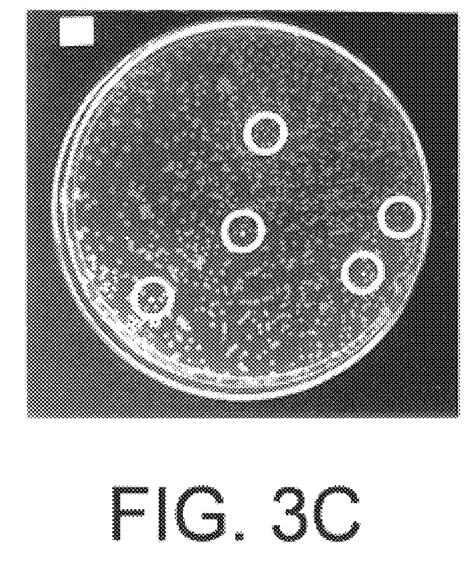
Figure 3D:
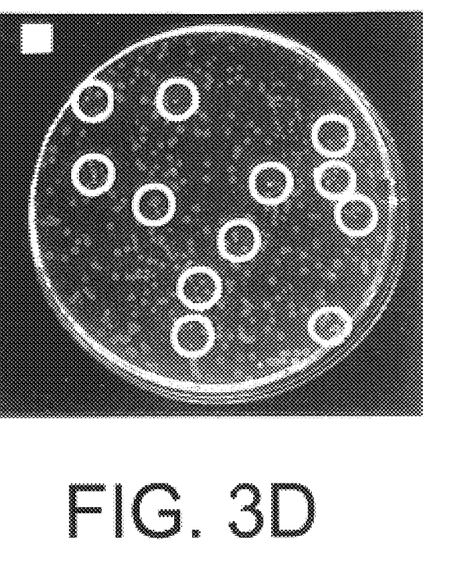

Correlation of the effect of mercuric ion on synthesome-driven in vitro DNA replication with that of intact cell DNA synthesis. (FIG. 2, Table II). To correlate the effect of mercuric ion on in vitro DNA replication with that of exponentially growing cell DNA synthesis, we examined the ability of intact HeLa cells to incorporate $^3$H-thymidine into DNA following their exposure to various concentrations of mercuric ion. Exponentially growing HeLa cells were incubated with increasing concentrations of mercuric ion for 2, 4, 6 or 3 hours. At each of these times the level of cell DNA synthesis was determined as described in the Materials and Methods. Relative to the no metal controls, the results depicted in FIG. 2 indicate that intact cell DNA synthesis was inhibited by greater than 80% at the higher concentrations of mercuric ion (10–100 μM) during the first two hours of the experiment; while lower concentrations of mercuric ion (1–10 μM) reduced intact cell DNA synthesis by 25–80%. The effect of mercuric ion on intact cell DNA synthesis occurs rapidly. Within 2 hours of exposure to 1 μM mercuric ion cellular DNA synthesis is reduced to 64% of that exhibited by control cells not exposed to the metal. In addition, exposure to 1 μM mercuric ion for an additional 2 hours decreased intact cell DNA synthesis to only 20% of the unexposed control cells (Table II). Higher concentrations of mercuric ion (10 μM and 100 μM) resulted in over an 85% inhibition in intact cells after only a 2 hour exposure to mercuric ion, and the level of inhibition closely parallels that observed after prolonged exposure to 1 μM mercuric ion, and exposure to mercuric ion for up to 4 hours at 10 μM and 100 μM concentrations of the metal (Table II). Exposure of cells to 100 μM mercuric ion for 8 hours completely abolished intact cell DNA synthesis. High concentrations of mercuric ion affect intact cell DNA synthesis in a manner which correlates with the effect of mercuric ion on synthesome-mediated in vitro DNA replication and DNA synthesome-associated DNA polymerase activity (FIGS. 1A and 1B).

In contrast to the inhibition of intact cell DNA synthesis by mercuric ion, the ability of intact cells to carry-out DNA synthesis was maintained in the presence of sodium chloride or zinc chloride, and did not decrease over the course of the entire experiment (Table II). This observation strongly suggests that the inhibition of intact cell DNA synthesis, like synthesome-driven DNA replication, was due solely to the mercuric ion, and not the divalent nature of the ion or the presence of the counterion.

TABLE II

Effect of sodium chloride, zinc chloride, mercuric chloride on intact cell DNA synthesis.

| salt | Percent Control Cell DNA Synthesis[a–d] | | | | | | | | |
|---|---|---|---|---|---|---|---|---|---|
| | 2 hours | | | 4 hours | | | 8 hours | | |
| $\mu$M | HgCl | NaCl | $ZnCl_2$ | HgCl | NaCl | $ZnCl_2$ | HgCl | NaCl | $ZnCl_2$ |
| 1 | 64 | 100 | 100 | 20 | 100 | 100 | 20 | 100 | 100 |
| 10 | 15 | 99 | 98 | 19 | 98 | 99 | 8 | 92 | 90 |
| 100 | 10 | 97 | 96 | 15 | 96 | 101 | 2 | 91 | 89 |

[a]Using the procedure described in the Materials and Methods intact cell DNA synthetic activity was determined by measruing the incorporation of $^3$H-thymidine into acid precipitated material
[b]The values reported represent the average of three independent experiments each of which was conducted using three tissue culture plates per salt condition indicated. These values deviated from the average by no more than 5%.
[c]Percent inhibition of the DNA synthetic activity was calculated relative to the control plates containing no exogenously added metal salts.
[d]Cell cultures were exposed to the range of salt concentrations for period of 2–8 hours prior to the addition of $^3$H-thymidine. At the times indicated on the table the media containing metal ion was replaced with fresh media lacking exogenously added metal ion, 5 $\mu$l $^3$H-thymidine was added to the cultures, and the cultures were incubated for 1 hour at 37° C. prior to acid precipitation of the cellular DNA.

Figure 4:
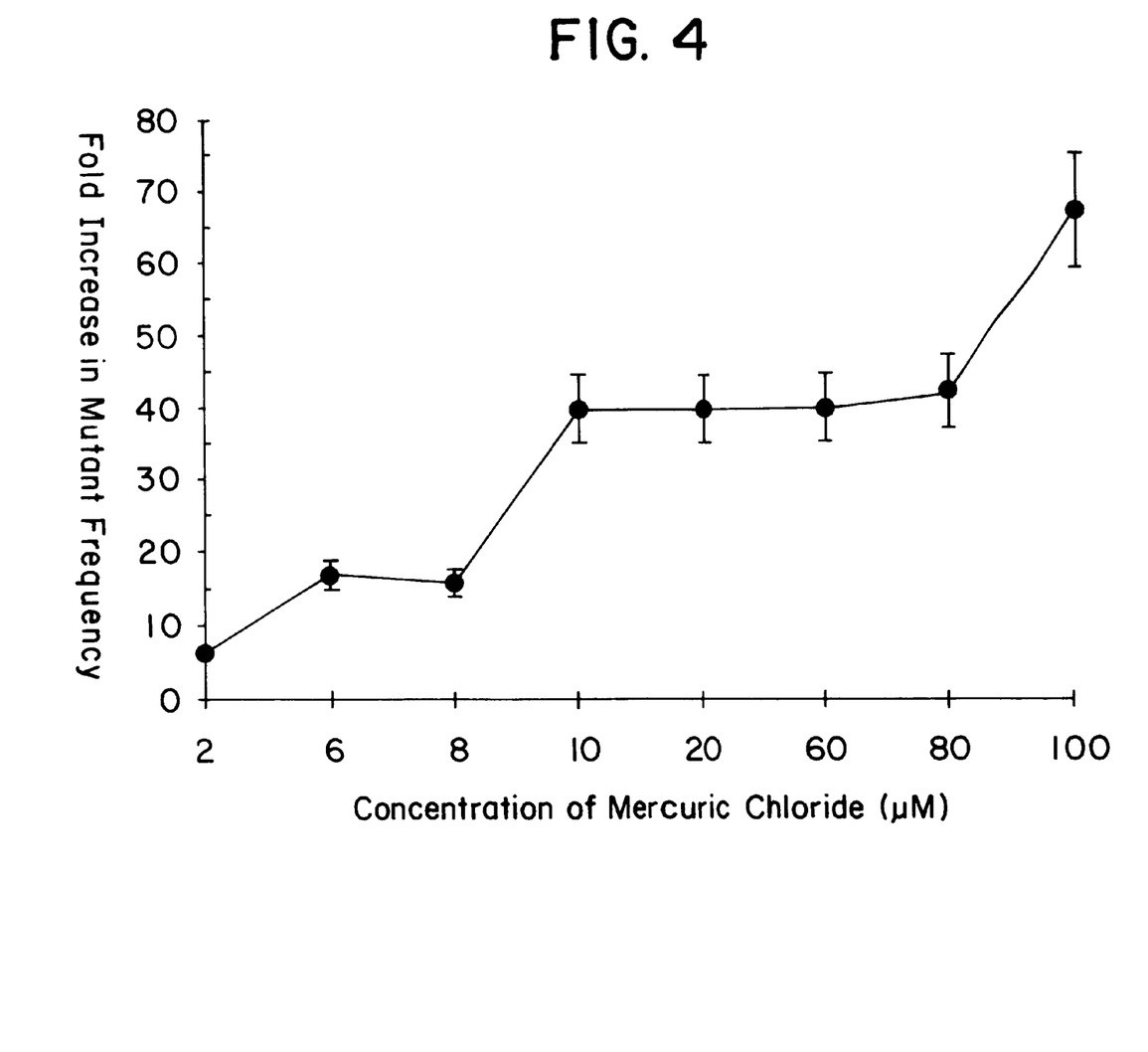
FIG. 4: Depicts the effect of a range of mercuric chloride ion concentrations on the frequency of mutations created during DNA synthesome mediated in vitro DNA replication. Bacterial colonies expressing the β-galactosidase gene on newly replicated plasmids isolated from DNA synthesome-mediated in vitro DNA replication were scored by the protocol described herein. The number of mutations normally produced by the DNA synthesome during the in vitro DNA replication reaction was determined by conducting assays in the absence of mercuric ion (4.4×10$^4$ mutants per 2×10$^8$ transformants=0.02%), and the value was used to calculate the fold increase in mutations created by the DNA synthesome during in vitro DNA replication reactions carried out in the presence of mercuric chloride. All reactions were normalized to the total number of transformants produced by a 100% transfection efficiency of the replicated DNA from each assay condition.

Physiologically attainable concentrations of mercuric ion decrease in vitro DNA replication fidelity. (FIGS. 3–4). In order to determine whether physiologically attainable concentrations of mercuric ion could alter the DNA synthetic product formed following exposure of the cellular DNA synthetic apparatus to very low concentrations of mercuric ion (i.e. between 1 $\mu$M and 10 $\mu$M) (Iyengar et al., 1978; Nakada and Imura, 1980; Svensson et al., 1995; Zaichick et al., 1995), we incubated the purified HeLa cell DNA synthesome with increasing concentrations of mercuric ion in our in vitro DNA replication fidelity assay (see Materials and Methods). FIG. 3 shows the results of plating bacteria transformed with the DpnI resistant products of the DNA synthesome-mediated in vitro DNA replication reaction. Concentrations of mercuric ion between 6–8 $\mu$M increased the number of detectable mutants by approximately 1.5–1.6 fold over the background mutation frequency arising in the DNA products isolated from reactions performed in the absence of any added mercuric ion (background: 4×10$^{-3}$ mutant colonies). Since this fidelity assay system is only able to detect mutations that affect the lac Z$\alpha$ gene and the gene-makes up approximately ⅓ of the nucleotide sequence of the pBK-CMV plasmid, and because we only score those mutations which produce a completely inactive β-galactosidase gene. A 1.5 fold increase in the mutation frequency represents a significant increase in the total number of mutations produced as a result of carrying out the DNA synthesome-mediated replication assay in the presence of mercuric ion. We also tested higher concentrations of mercuric ion (10 $\mu$M–80 $\mu$M mercuric ion), for their ability to reduce the in vitro DNA synthetic fidelity of the DNA synthesome. We observed mutation frequencies that were approximately 2.60–2.85 fold higher than background (FIG. 4). The highest concentration of mercuric ion (100 $\mu$M) tested in the fidelity assay resulted in a 4.2 fold increase in replication errors over background levels determined for reactions run in the absence of mercuric ion. The results of our fidelity analysis clearly indicate that the mutation frequency increases as a function of increasing mercuric ion concentration.

DISCUSSION

In this report we have demonstrated that mercuric ion selectively inhibits in vitro synthesome-mediated SV40 DNA replication. Our experimental results suggest that the synthesome-mediated DNA replication system may be a useful model for examining the effect of mercuric ion on DNA synthesis. Mercuric ion inhibits in vitro DNA replication in a concentration-dependent manner that closely correlates with that observed in intact HeLa cells. In intact cells, DNA synthesis was rapidly and dramatically inhibited in the presence of high concentrations (10–100 $\mu$M) of mercuric ion, while lower concentrations of the metal (1–10 $\mu$M) were observed to inhibit DNA synthesis to a much lower degree. The inhibition of DNA synthesis observed in intact cells following prolonged exposure to the metal ion could be the result of the interaction of mercuric ion with other cellular processes that support intact cell DINA synthesis. The close correlation between the effects of mercuric ion on intact cell DNA synthesis and synthesome-mediated in vitro DNA replication over the time frame of the in vitro assays suggests that mercuric ion directly affects the cellular DNA replication machinery.

It has been previously reported that mercuric ion inhibits the mammalian DNA polymerase activity present in whole-cell extracts or in purified enzyme preparations (Williams et al., 1986; Robinson et al., 1984; Rivedal and Sanner, 1981) at higher concentrations of the metal (i.e., greater than 10 $\mu$M mercuric ion). This report supports the literature evidence, while further clarifying the picture by demonstrating the effect of mercuric ion on the intact multiprotein DNA replication machinery of the cell. Mercuric ion was demonstrated to significantly inhibit synthesome-associated DNA polymerase activity. The inhibition of the DNA polymerase activity correlated well with the observed effect of mercuric ion on synthesome-mediated in vitro DNA replication, as well as its ability to decrease intact cell DNA synthesis. Our studies, together with the earlier reports of Williams et al. (1986), Robinson et al. (1984), and Rivedal and Sanner (1981), suggest that mercuric ion (at concentrations above 10 $\mu$M) actively inhibits the elongation stage of DNA replication.

Although our data suggests that mercuric ion is inhibitory of DNA synthesis, and the literature reports that mercuric ion is cytotoxic and has diverse effects on cellular function, the concentrations at which these effects are found (greater than 10 µM) are greater than would normally be found physiologically (Iyengar et al., 1987; Nakada and Imura, 1980; Zaichick et al., 1995). Because the literature reports that clinical cases involving mercury exposure are largely due chronic exposure of the individual to chronic exposure to low concentrations of mercuric ion (Zaichick et al, 1995), we also investigated the effects of low concentrations of mercuric ion (2, 4, 8, 10 µM) on DNA replication fidelity. By utilizing the intact multiprotein DNA replication apparatus of the cell (the DNA synthesome) we were able to detect an increase in the number of mutations produced by the synthesome in the presence of low concentrations of mercuric ion. The results presented in this paper suggest that the DNA replication machinery of the cell has a role in mediating the observed mutagenic potential of mercuric ion (Ariza and Williams,1996; Christie et al., 1984) and perhaps to the observed cytotoxic and carcinogenic effects observed in patients chronically exposed to low doses of mercuric ion (Zaichick et al, 1995). Taken together our results suggest that the isolated human cell DNA synthesome may be a novel model system for studies examining how mercuric ion, and potentially other heavy metal ions, affect DNA synthesis.

ACKNOWLEDGMENTS

This work was supported by awards to RH from the American Cancer Society/Maryland Division, and the University of Maryland Designated Research Initiative Fund, and by an award to LM from the National Cancer Institute (CA57350, CA65754). JWS was supported by a predoctoral fellowship from the U. S. Army Breast Cancer Research Program and an award from Sigma Xi.

REFERENCES

Applegren, N. B., Hickey, R. J. Kleinschmidt, A. M., Zhou, Q. Q., Coll, J., Wills, P., Swaby, R, Wie, Y-T, Quan J. Y., Lee, M. Y. W. T., and Malkas, L. (1995). Further characterization of the human cell multiprotein DNA replication complex. J. Cell. Biochem. 59, 91–97.

Ariza, M. E. and Williams, M. V. (1996). Mutagenesis of AS52 cells by low concentrations of lead (II) and mercury (II). Environmental and Molecular Mutagenesis: 27(1), 30–3.

Bell, S. P., Kobayashi, R., and Stillman, B. (1993). Yeast origin recognition complex functions in transcription silencing and DNA replication. Science 262, 1844–1848.

Caldentey, J., Blanco, L., Savilahti, H., Bamford, D. H., Salas, M. (1992). In vitro replication of bacteriophage PRD1 DNA. Metal activation of protein-primed initiation and DNA elongation. Nucleic Acids Res. 20, 3971–3976.

Cantoni, O., Christie, N. T., Swann, A., Drath, D. B., Costa, M. (1984) Mechanism of $HgCl_2$ cytotoxicity in cultured mammalian cells. Mol. Pharmacol. 26, 360–368.

Casto, B. C., Myers, J. D., and DiPaolo, J. A. (1979) Enhancement of viral transformation for evaluation of the carcinogenic or mutagenic potential of inorganic metal salts. Cancer Res. 39, 193–197.

Christie, N. T., Cantoni, O., Evans, R. M., Meyn R. E., Costa, M. (1984). Use of mammalian DNA repair deficient mutants to assess the effects of toxic metal compounds on DNA Biochem. Pharmacol. 33, 1161–1670.

Coll, J. M, Sekowski, J. W., Hickey, R. J., Schnaper, L., Wei., Y., Brodie, A., Syvaoja, J., and Malkas, L. H. (1996) The human breast cell DNA synthesome: its purification from tumor tissue and cell culture. Oncol. Res., in press.

DePamphilis, M. and Bradley, M. (1986). Replication of SV40 and polyoma virus chromosomes. In, The Papovaviridae, volume 1: The Polyomavirus (Salzman, N. P., ed.), pp. 99–246. Plenum Press, New York.

Dermody, J. J., Lawlor, K. G., Du, H., Wojcik, B., Jha, K. K, Malkas, L., Hickey, R, Baril, E. F., Ozer, H. L. (1988). Polyomavirus DNA synthesis in vitro: studies with CHO, 3T3 and their tsDNA mutants. Cancer Cells 6, 95–100.

Goldberg, R. L., Kaplan, S. R., and Fuller, G. C., (1983) Effect of heavy metals on human rheumatoid synovial cell proliferation and collagen synthesis. Biochem. Pharmacol., 321, 2763–2766.

Horwitz, S. B., Change, C. K., and Grollman, A. P. (1971). Studies on camptothecin: effects on nucleic acid and protein synthesis. Mol. Pharmacol. 7, 632–644.

Hsie, A. W., Johnson, M. P., and Couch, D. B. (1979). Quantitative mammalian cell mutagenesis and a preliminary study of the mutagenic potential of metallic compounds. In, Trace Metals in Health and Disease (Kharasch, N., ed.), pp. 5–69. Raven Press, New York Hutchinson, F., Macleod, T. M., and Raffle, E. J. (1976) Leukocyte aggregation and lymphocyte transformation induced by mercuric chloride. Clin. Exp. Immunol. 2, 531–533.

Iyengar, G. V., Kollmer W. E., and Bowen, H. J. M. (1978). The elemental composition of human tissue and body fluids. Verlag Chemie: Weinheim.

Leonard, A., Jacquet, P., Lauwers, R. R. (1983) Mutatgenicity and teratogenicity of mercury compounds. Mutation Res. 114, 1–18.

Lin, S, Hickey, R. J., and Malka, L. H. (1996) A multiprotein DNA replication Complex Isolated from Human Leukemia Cells Is Competent for DNA Synthesis an in vitro/Leukemia Research (in press).

Malkas, L. H., Hickey, R. J., Li, C.-J., Pederson, N., and Baril, E. F. (1990). A 21S enzyme complex from HeLa cells that functions in simian virus 40 DNA replication in vitro. Biochemistry 29, 6362–6374.

Micklem, G., Rowley, A., Harwood, J., Nasmyth, K. and Diffley, J. F. X. (1993) Yeast origin recognition complex is involved in DNA replication and transcriptional silencing. Nature 366, 87–91.

Murakami, Y., Eki, T., Yamada, M., Prives, C., and Hurwitz, J. (1986): Species-specific in vitro synthesis of DNA containing the polyomavirus origin of replication. Proc. Natl. Acad. Sci. U.S.A. 983, 6347–6351.

Nakada, S., and Imura, N. (1980) Stimulation of DNA synthesis and pyrimidine deoxyribonucloside transport systems in mouse glioma and mouse neuroblastoma cells by inorganic mercury. Toxicol. Appl. Pharmacol. 53, 24–28.

Oberly, T. J., Piper, C. E., and McDonald, D. S. (1982). Mutagenicity of metal salts in the 151784 mouse lymphoma assay. J. Toxicol. Environ. Health 9, 367–376.

Rivedal, E. and Sanner, T. (1981). Metal salts as promoters of in vitro morphological transformation of hamster embryo cells induced by benzopyrene. Cancer Res. 41, 950–953.

Robinson, S. H., Cantoni, O., and Costa, M. (1984). Analysis of metal-induced DNA lesions and DNA repair replication in mammalian cells. Mutat. Res. 131, 173–181.

Sambrook, J., Fritsch, E., & Maniatis, T., eds. (1989) Commonly Used Techniques in Molecular Cloning. In: *Molecular Cloning: A Laboratory Manual,* 2nd Edition, p.E1–E28. Cold Spring Harbor Laboratory Press, Cold Spring Harbor, N.Y.

Simianis, V. and Lane, D. P. (1985). An immunoaffinity purification procedure for SV40 large T-antigen. Virology 144, 88–100.

Stacey, N. H. and Kappus, H. (1982) Cellular toxicity and lipid peroxidation in response to mercury. Toxicol. Appl. Pharmacol. 63, 29–35.

Stillman, B. W. and Gluzman, Y. (1985): Replication and supercoiling of simian virus 40 DNA in cell extracts from human cells. Mol. Cell. Biol. 5, 2051–2060.

Svensson, B-G., Nilsson, A., Jonsson, E., Schutz, A., Akesson, B., Hagmar, L. (1995) Fish consumption and exposure to persistent organochloride compounds, mercury, selenium, and methylamines among Swedish fishermen. Scand. J. Work Environ. Health 21, 96–105.

Umeda, M., Saito, K., Hirose, K., and Saito, M. (1969) Cytotoxic effect of inorganic phenyl, and alkyl mercuric compounds on HeLa cells. Jpn. J. Exp. Med. 39, 47–58.

Umeda, M. and Nishimura, M. (1979). Inducibility of chromosomal aberrations by metal compounds in cultured mammalian cells. Mutation Res. 67,221–229.

Williams, M. N. and Crothers, D. M. (1975) The binding kinetics of mercury (II) to polyribonucleotides. Biochemistry 14, 1944–1950.

Williams, M. V., Winters, T., and Waddell, K. S. (1986) In vivo effects of mercury (II) on deoxyuridine triphosphate nucleotidohydrolase, DNA polymerase ($\alpha$, $\beta$), and uracil-DNA glycosylase activities in cultured human cells: relationship to DNA damage, DNA repair, and cytotoxicity. Molecular Pharmacology 31, 200–207.

Wu, Y., Hickey, R., Lawlor, K., et al. (1994). A 17S form of DNA polymerase from mouse cells mediates the in vitro replication of polyomavirus DNA. J. Cell. Biochem. 54, 32–46.

Zaichick, V. Y., Tsyb, A. F., Vtyurin, B. M. (1995) Trace Elements and Thyroid Cancer. Analyst 20, 817–821.

Roberts, J. D., and Kunkel, T. A. (1988). The fidelity of a human cell DNA replication complex, Proc. Natl. Acad. Sci. U.S.A. 85, 7064–7068.

The examples discussed herein are provided for illustrative purposes only, and are in no way intended to limit the scope of the present invention.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

We claim:

1. A method for identifying whether a test compound alters the fidelity of a multi-protein DNA replication complex comprising:
   (A) exposing said test compound to (i) a purified multi-protein DNA replication complex isolated from a mammalian cell and capable of supporting all phases of origin-specific DNA replication in vitro, and (ii) a DNA template comprising an origin of replication recognized by said complex, under conditions to achieve replication of said DNA template;
   (B) detecting DNA mutations in the replicated DNA template obtained in step (A) and determining the frequency of DNA mutation in said replicated DNA template; and
   (C) comparing the frequency of DNA mutation occurrence in the presence of said test compound with the frequency of spontaneous DNA mutation occurrence and with the frequency of DNA mutation occurrence in a negative control.

2. The method of claim 1, wherein detecting in step (B) comprises the steps of:
   (i) transfecting a host cell with said replicated DNA template, wherein said DNA template encodes a protein under the control of a promoter operable in said host cell; and
   (ii) assaying for expression, by said host cell, of protein encoded by said replicated DNA template.

3. The method of claim 2, wherein said host cell is a bacteria.

4. The method of claim 3, wherein said bacteria is *E. coli*.

5. The method of claim 1, wherein said origin of replication is an SV40 origin of replication.

6. The method of claim 1, wherein said DNA template is plasmid pBK-CMV.

7. The method of claim 1, wherein said DNA replication complex is isolated from murine cells.

8. The method of claim 1, wherein said DNA replication complex is isolated from human cells.

9. The method of claim 8, wherein said human cells are selected from the group consisting of HeLa cells, primary human breast tumor cells, human breast tissue cells, human leukemia cells, and human pancreatic cells.

10. The method of claim 1, wherein said DNA template encodes the lacZ$\alpha$ gene.

11. The method of claim 1, wherein said test compound is selected from the group consisting of ionic mercury and ionic cadmium.

* * * * *